United States Patent
Chornenky et al.

(10) Patent No.: US 6,799,075 B1
(45) Date of Patent: *Sep. 28, 2004

(54) X-RAY CATHETER

(75) Inventors: Victor I. Chornenky, Minnetonka, MN (US); Michael R. Forman, St. Paul, MN (US)

(73) Assignee: Medtronic Ave, Inc., Santa Rosa, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 372 days.

(21) Appl. No.: 08/701,764

(22) Filed: Aug. 22, 1996

Related U.S. Application Data

(60) Provisional application No. 60/006,708, filed on Nov. 14, 1995, and provisional application No. 60/002,722, filed on Aug. 24, 1995.

(51) Int. Cl.[7] .............................................. A61B 18/18
(52) U.S. Cl. .......................... 607/117; 607/100; 600/9; 378/65; 378/121; 378/136
(58) Field of Search ........................... 600/1–3, 9, 426; 607/100, 101, 117; 378/65, 119, 121, 122, 136, 143, 197, 198; 250/522.1

(56) References Cited

U.S. PATENT DOCUMENTS

| | | |
|---|---|---|
| 1,786,373 A | 12/1930 | Walker |
| 1,881,448 A | 10/1932 | Forde et al. |
| 2,467,812 A | 4/1949 | Clapp |
| 2,766,385 A | 10/1956 | Herrnring et al. |
| 3,005,096 A | 10/1961 | Chynoweth |
| 3,073,960 A | 1/1963 | Guentner et al. |

(List continued on next page.)

FOREIGN PATENT DOCUMENTS

| | | |
|---|---|---|
| DE | 2054738 | 5/1972 |
| DE | 26 08 418 | 9/1977 |
| JP | 58-145098 A | 8/1983 |
| RU | 814331 | 3/1981 |
| WO | WO 95/20241 | 7/1995 |
| WO | WO 96/02059 | 1/1996 |

OTHER PUBLICATIONS

Brochure: "Dunlee DL–1 Stationary Anode Insert", Dunlee Corporation, Bellwood, IL 60104, Jun. 1972.
Brady, et al., *Gynecologic Oncology*, 2:314–323 (1974).
Condado, et al., 1 page, *Discoveries in Radiation for Restenosis*, Emory University School of Medicine (Jan. 1996).
Fischell, et al., *Circulation*, 90(6): 2956–2963 (Dec. 1994).
Geissler, et al., *Physics Letters A*, 176:387–392 (1993).
Gundel, et al., *Nuclear Instruments and Methods in Physics Research*, A280:1–6 (1989).

(List continued on next page.)

*Primary Examiner*—David M. Shay
(74) *Attorney, Agent, or Firm*—Ingrassia Fisher & Lorenz, P.C.

(57) ABSTRACT

A catheter for emitting radiation is disclosed, comprising a catheter shaft and an x-ray unit attached to the distal end of the catheter shaft. The x-ray unit comprises an anode and a cathode coupled to an insulator to define a vacuum chamber. The cathode is preferably a field emission cathode of graphite or graphite coated with titanium carbide, for example. The anode is preferably tungsten and the insulator is preferably pyrolytic boron nitride. The x-ray unit is preferably coupled to a voltage source through a coaxial cable. The anode is preferably a heavy metal such as tungsten. The cathode may also be a ferroelectric material. The x-ray unit can have a diameter less than about 4 mm and a length less than about 15 mm. Methods of use of the catheter are also disclosed. The catheter of the present invention can be used to irradiate the site of an angioplasty procedure to prevent restenosis. It can also be used to treat other conditions in any vessel, lumen or cavity of the body.

33 Claims, 11 Drawing Sheets

U.S. PATENT DOCUMENTS

| | | |
|---|---|---|
| 3,125,679 A | 3/1964 | Ohde et al. |
| 3,256,439 A | 6/1966 | Dyke et al. |
| 3,348,051 A | 10/1967 | Weighart et al. |
| 3,381,129 A | 4/1968 | Duftschmid |
| 3,388,314 A | 6/1968 | Gould |
| 3,484,721 A | 12/1969 | Bond et al. |
| 3,508,059 A | 4/1970 | Vanderpool |
| 3,538,919 A | 11/1970 | Meyer |
| 3,564,251 A | 2/1971 | Youmans |
| 3,617,939 A | 11/1971 | Bond et al. |
| 3,628,021 A | 12/1971 | MacDonald |
| 3,691,417 A | 9/1972 | Gralenski |
| 3,714,486 A | 1/1973 | McCrary |
| 3,752,990 A | 8/1973 | Fischer |
| 3,866,050 A | 2/1975 | Whitfield |
| 3,878,394 A | 4/1975 | Golden |
| 3,883,760 A | 5/1975 | Cunningham, Jr. |
| 3,920,999 A | 11/1975 | Drexler et al. |
| 3,970,884 A | 7/1976 | Golden |
| 3,987,281 A | 10/1976 | Hodes |
| 4,058,486 A | 11/1977 | Mallozzi et al. |
| 4,060,731 A | 11/1977 | Rissi |
| 4,097,759 A | 6/1978 | Furbee et al. |
| 4,104,526 A | 8/1978 | Albert |
| 4,104,530 A | 8/1978 | Weiss |
| 4,104,531 A | 8/1978 | Weiss |
| 4,104,532 A | 8/1978 | Weiss |
| 4,109,154 A | 8/1978 | Taumann |
| 4,117,334 A | 9/1978 | Strauts |
| 4,143,275 A | 3/1979 | Mallozzi et al. |
| 4,158,138 A | 6/1979 | Hellstrom |
| 4,163,901 A | 8/1979 | Azam et al. |
| 4,191,193 A | 3/1980 | Seo |
| 4,344,181 A | 8/1982 | Baecklund |
| 4,359,660 A | 11/1982 | Smith et al. |
| 4,368,538 A | 1/1983 | McCorkle |
| 4,563,769 A | 1/1986 | Madsen |
| 4,607,380 A | 8/1986 | Oliver |
| 4,636,195 A | 1/1987 | Wolinsky |
| 4,646,338 A | 2/1987 | Skillicorn |
| 4,669,467 A | 6/1987 | Willett et al. |
| 4,670,894 A | 6/1987 | Birnbach et al. |
| 4,694,480 A | 9/1987 | Skillicorn |
| 4,701,941 A | 10/1987 | Szirmai et al. |
| 4,702,228 A | 10/1987 | Russell, Jr. et al. |
| 4,715,054 A | 12/1987 | Kato et al. |
| 4,763,671 A | 8/1988 | Goffinet |
| 4,789,997 A | 12/1988 | Madsen et al. |
| 4,794,931 A | 1/1989 | Yock |
| 4,800,581 A | 1/1989 | Kujirai et al. |
| 4,824,436 A | 4/1989 | Wolinsky |
| 4,856,036 A | 8/1989 | Malcolm et al. |
| 4,913,142 A | 4/1990 | Kittrell et al. |
| 4,924,485 A | 5/1990 | Hoeberling |
| 4,966,596 A | 10/1990 | Kuntz et al. |
| 4,976,266 A | 12/1990 | Huffman et al. |
| 4,979,199 A | 12/1990 | Cueman et al. |
| 5,042,486 A | 8/1991 | Pfeiler et al. |
| 5,059,166 A | 10/1991 | Fischell et al. |
| 5,077,771 A | 12/1991 | Skillicorn et al. |
| 5,087,244 A | 2/1992 | Wolinsky et al. |
| 5,090,043 A | 2/1992 | Parker et al. |
| 5,099,845 A | 3/1992 | Besz et al. |
| 5,101,422 A | 3/1992 | Thiel et al. |
| 5,106,360 A | 4/1992 | Ishiwara et al. |
| 5,148,463 A | 9/1992 | Woodruff et al. |
| 5,153,900 A | 10/1992 | Nomikos et al. |
| 5,165,093 A | 11/1992 | Miller et al. |
| 5,199,939 A | 4/1993 | Dake et al. |
| 5,222,116 A | 6/1993 | Eloff et al. |
| 5,228,176 A | 7/1993 | Bui et al. |
| RE34,421 E | 10/1993 | Parker et al. |
| 5,264,801 A | 11/1993 | DeCou, Jr. et al. |
| 5,290,275 A | 3/1994 | Kittrell et al. |
| 5,313,949 A | 5/1994 | Yock |
| 5,313,950 A | 5/1994 | Ishikawa et al. |
| 5,364,336 A | 11/1994 | Carr |
| 5,369,679 A | 11/1994 | Sliski et al. |
| 5,402,790 A | 4/1995 | Jang et al. |
| 5,414,748 A | 5/1995 | Upadhya |
| 5,422,926 A | 6/1995 | Smith et al. |
| 5,425,735 A | 6/1995 | Rosen et al. |
| 5,428,658 A | 6/1995 | Oettinger et al. |
| 5,437,277 A | 8/1995 | Dumoulin et al. |
| 5,442,678 A | 8/1995 | Dinsmore et al. |
| 5,444,254 A | 8/1995 | Thomson |
| 5,452,720 A | 9/1995 | Smith et al. |
| 5,453,575 A | 9/1995 | O'Donnell et al. |
| 5,454,809 A | 10/1995 | Janssen |
| 5,465,732 A | 11/1995 | Abele |
| 5,469,490 A | 11/1995 | Golden et al. |
| 5,474,075 A | 12/1995 | Goldberg et al. |
| 5,503,613 A | 4/1996 | Weinberger |
| 5,504,799 A | 4/1996 | Suzuki |
| 5,511,107 A | 4/1996 | Sliski |
| 5,528,652 A | 6/1996 | Smith et al. |
| 5,566,221 A | 10/1996 | Smith et al. |
| 5,621,780 A | 4/1997 | Smith et al. |
| 5,623,139 A | 4/1997 | Sliski |
| 5,635,709 A | 6/1997 | Sliski et al. |
| 5,729,583 A * | 3/1998 | Tang et al. ............... 378/122 |

OTHER PUBLICATIONS

Gundel, et al., *J. Appl. Phys.*, 69:(2):975–982 (Jan. 1991).

Hehrlein, et al., *Circulation*, 92(6):1570–1575 (Sep. 1995).

Papillon, *Diseases of the Colon & Rectum*, 27(11):695–700 (Nov. 1984).

March, et al., *Circulation*, 87(1):184–191 (Jan. 1993).

Matsuda, et al., *Journal of Materials Science*, 21:649–658 (1986).

Phillips, *Radiology*, 90(3):525–531 (Mar. 1968).

Pouch, et al., *Materials Science Forum*, 54&55:141–152 (1990).

Riege, *Nucl. Inst. and Meth. in Phys. Res.*, A340:80–89 (1994).

Schwartz, et al., *JACC*, 19(5):1106–1113 (Apr. 1992).

Soares, et al., *Nuclear Technology Publishing*, 47(174):367–372 (1993).

Strickland, *Clinical Radiology—The J. of the Faculty of Radiologists*, XVI(1–4):112–118 (Jan. to Oct. 1965).

Verin, et al., *Circulation*, 92:(8):2284–2290 (Oct. 1995).

Wang, et al., *Int. J. Radiation Oncology Biol. Phys.*, 9(8):1185–1189 (Aug. 1983).

Waksman, et al., *Circulation*, 92(6):1383–1386 (Sep. 1995).

Waksman, et al., *Circulation*, 92(10): 3025–3031 (Nov. 1995).

Waksman, et al., *Circulation*, 91(5):1533–1539 (Mar. 1995).

Wiedermann, et al., *JACC*, 23(6): 1491–1498 (May 1994).

Wiedermann, et al., *JACC*, 25(6):1451–1456 (May 1995).

Wiedermann, et al., "Effects of high–dose intracoronary irradiation on vasomotor function and smooth muscle histopathology", pp.H125–H132 (1994).

* cited by examiner

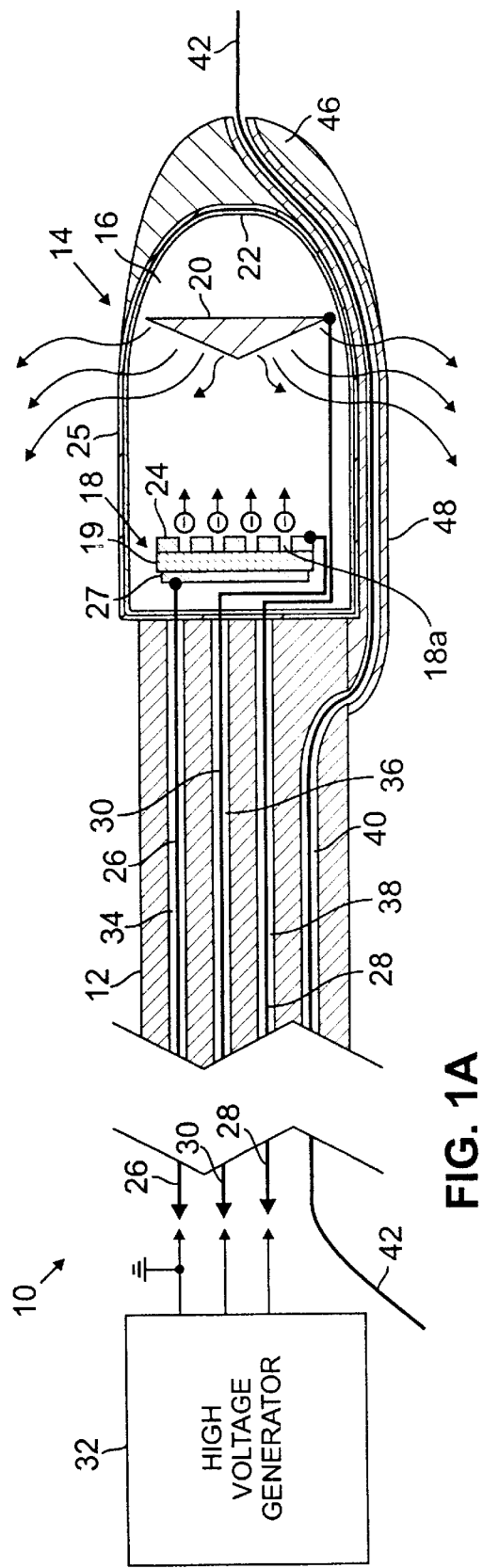
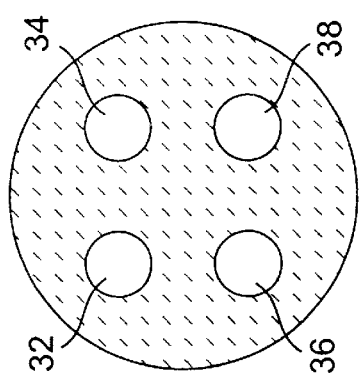
FIG. 1A
FIG. 1B

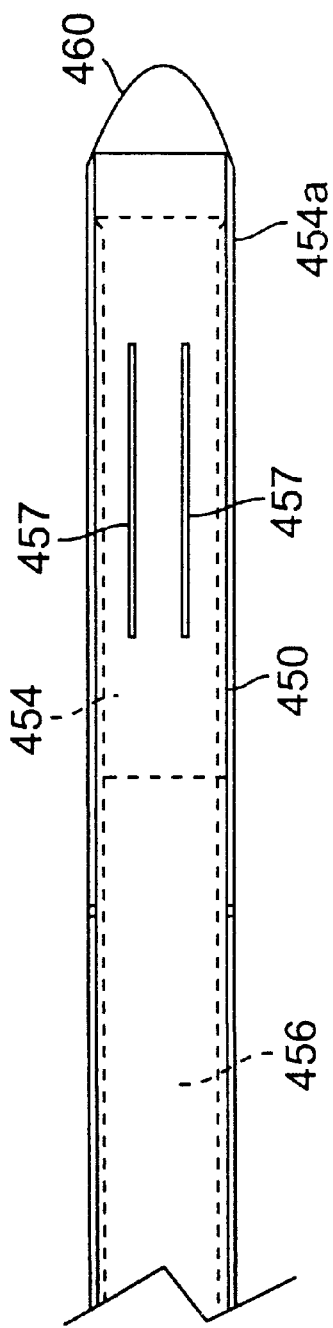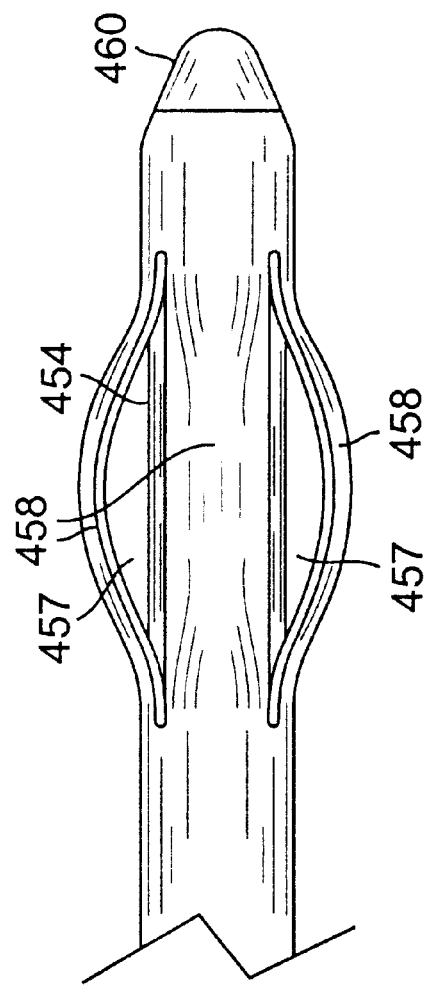

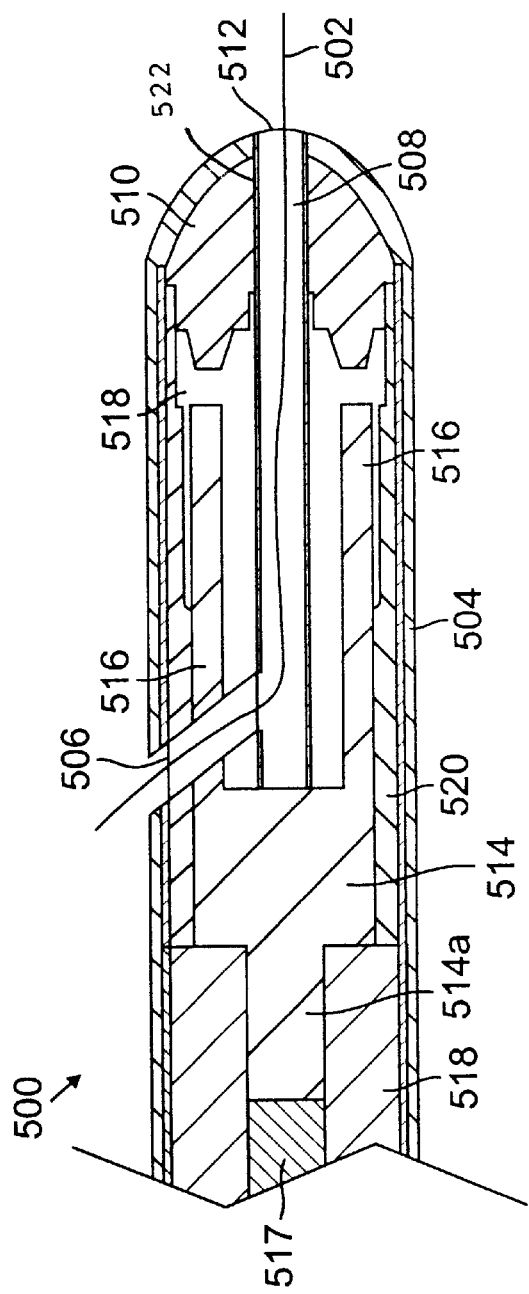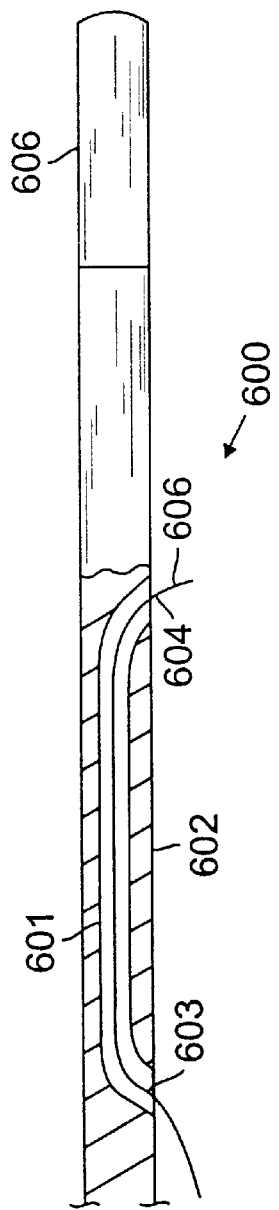

X-RAY CATHETER

This application claims the benefit of U.S. Provisional Application Nos. 60/006,708 filed Nov. 14, 1995, and No. 60/002,722 filed Aug. 24, 1995.

FIELD OF THE INVENTION

The present invention relates generally to catheters and, more particularly, to catheters for irradiating vessels, lumens or cavities of a body, such as cardiovascular tissue to reduce the incidence of restenosis, and to treat other conditions.

BACKGROUND OF THE INVENTION

Restenosis of an artery or vein after percutaneous transluminal coronary angioplasty (PTCA) or percutaneous transluminal angioplasty (PTA) occurs in about one-third of the procedures, requiring the procedure to be repeated. Various types of drugs or other agents are being investigated for use in preventing restenosis. Heparin, an anticoagulant and inhibitor of arterial smooth muscle proliferation, is one such drug. Dexamethasone may also prevent smooth muscle proliferation. Integralin, which prevents aggregation of platelets, may also be useful. Other anticoagulants and antiproliferative agents are being investigated for efficacy, as well. Such drugs can be delivered before or after the angioplasty procedure. The delivery of lytic agents such as urokinase, streptokinase and recombinant tissue type plasminogen activator (rTPA) to dissolve thrombi in arteries and veins is also being investigated.

Because of blood flow through the artery, drugs delivered to the site of an angioplasty procedure, for example, can be rapidly dissipated and removed from the site before they can be sufficiently absorbed to be effective. Catheters have therefore been developed to directly drive the drug into the desired site through a balloon or to maintain the delivered drug agent proximate the desired site by isolating the region with occlusion balloons. See, for example, U.S. Pat. Nos. 5,087,244, 4,824,436, and 4,636,195, to Wolinsky.

The use of sufficient pressures to drive the drug into the tissue or plaque, however, may damage the arterial wall. Passive delivery into a region isolated by occlusions balloons, on the other hand, is slow and may not enable sufficient absorption of the medication. Passive delivery can be particularly inappropriate for drug delivery in an artery because blood flow can only be occluded in an artery for a limited period of time.

Stents have also been used after angioplasty to prevent an opened blood vessel from closing. The use of stents, however, has only shown a small decrease in the incidence of restenosis. Stents are also difficult to properly position and are expensive.

The use of radiation has also been investigated to reduce restenosis after PTCA or PTA. One technique is Photodynamic Therapy (PDT), wherein photosensitive drugs delivered to the angioplasty site are activated by irradiation with ultraviolet (UV) or visible light.

Another approach was to expose vascular tissue to UV light within a wavelength band of DNA absorption (240–280 nm) by a laser to disable or destroy the DNA of the tissue. This would impair or destroy the ability of the vascular tissue to proliferate. This approach had only limited success, however, because UV light does not penetrate vascular tissue sufficiently to prevent proliferation or migration of smooth muscle tissue.

Beta-irradiation of the vessel after angioplasty with radioactive guide wires or implanted stents is another technique.

U.S. Pat. No. 5,199,939 to Dake et al., for example, discloses a catheter with radioactive pellets at its distal end to irradiate the site of an angioplasty procedure to prevent restenosis. The need for a radioactive source in the catheter lab, however, requires protection against radioactive hazards to personnel and costly compliance with regulations. It is also difficult to control the depth of penetration of the radiation by this method.

U.S. Pat. No. 4,143,275 to Mallozzi et al., discloses an x-ray device for delivering radiation to remote locations of the human body such as the interior of the heart. The x-ray radiation is generated by irradiating a target material, such as iron, calcium, chromium, nickel, aluminum, lead, tungsten or gold, by a laser to vaporize the metal. X-ray radiation is emitted from the ionized vapor plasma. The target is located outside the body and the x-rays are directed to a desired location within the body through a hollow guide. The patent discusses use of such a device to produce radiographs, to irradiate tumors or to alter tissue. It is believed, however, that x-ray radiation generated by this method would have photon energy of about 1–2 KeV at best, which is too low to penetrate biological tissue deeper than about 20–30 microns. In addition, the patent does not disclose how to produce a guide which is both flexible enough to be advanced through the cardiovascular system and able to transmit adequate x-ray radiation to an intended site without excessive losses.

U.S. Pat. No. 5,153,900 to Nomikos, et al., discloses a miniaturized low power x-ray source for interstitial insertion for the treatment of tumors. The device comprises a housing with an elongated cylindrical, rigid probe. An anode and cathode are located in the housing and a target is located at the distal end of the probe. The cathode and target must lie along the same axis. Electrons emitted by the cathode, which can be a thermionic emitter or a photocathode, impinge on the target, causing the emission of x-ray radiation. A rigid probe is unsuitable for use in the cardiovascular system.

U.S. Pat. No. 5,428,658 to Oettinger, et al., a continuation of the patent to Nomikos, discussed above, discloses a flexible probe comprising a flexible optical fiber within a metallic tube. The optical fiber has a photoemissive coating at its terminal end. A target is located distal to the terminal end of the optical fiber, within an evacuated shell. The flexible probe is said to enable threading down a pathway, such as the trachea, or around structures, such as nerves or blood vessels. Such a device is not sufficiently flexible for advancement through the cardiovascular system, nor is it believed that such a device can be made small enough to access the site of a PTCA procedure.

U.S. Pat. No. Re 34,421 to Parker, et al. discloses an x-ray microtube comprising a glass tube having a diameter less than one inch, for insertion into the body for treating a tumor. While asserting that the diameter can be as small as ⅛ inch, Parker does not address any of the problems associated with such a small device, such as electrical flashover. It is questionable whether such a device could be made small enough to access the site of a PTCA procedure, and still function. Glass also has too high a coefficient of absorption of x-ray radiation to enable delivery of sufficient x-ray radiation to prevent restenosis in a reasonable period of time. Parker also does not disclose any way to advance its x-ray source through the cardiovascular system, or any other channel of the body.

SUMMARY OF THE INVENTION

In accordance with a preferred embodiment of the present invention, an x-ray catheter is disclosed which is small and flexible enough to access an intended site within a vascular system of the body, such as the coronary arteries of the cardiovascular system. The x-ray catheter can operate at the high voltages required for generating x-ray radiation of an effective spectrum for preventing restenosis and treating other conditions. It also has walls highly transmissive to x-ray radiation so that an effective dosage can be delivered in a short period of time.

In accordance with the present invention, a catheter for emitting x-ray radiation is disclosed comprising a flexible catheter shaft having a distal end and an x-ray unit coupled to the distal end. The x-ray unit comprises an anode, a cathode and an insulator, wherein the anode and cathode are coupled to the insulator to define a vacuum chamber. The insulator is preferably pyrolytic boron nitride, which is highly transmissive to x-ray radiation. The cathode is preferably a field emission cathode of graphite, graphite coated with titanium carbide, or other carbides. The cathode can also comprise silicon and the x-ray unit can include a grid. The cathode can be a ferroelectric material, as well. The anode is preferably tungsten. The catheter shaft is preferably a coaxial cable. A guide wire may be provided extending through the catheter shaft, partially through the catheter shaft or partially through the x-ray unit, in a rapid exchange configuration. The catheter further preferably comprises a means for centering the x-ray unit within a lumen.

In accordance with another embodiment of the invention, an x-ray catheter is disclosed comprising a flexible catheter shaft for being advanced through lumens of a vascular system.

Another embodiment of the present invention comprises an x-ray generating unit having a diameter less than about 4 mm.

Yet another embodiment of the present invention comprises a catheter shaft, an x-ray generating unit and means for centering the x-ray generating unit within the lumen.

A method is also disclosed in accordance with the present invention for preventing restenosis of a lumen or treating other conditions, comprising advancing an x-ray catheter through a lumen to a first location adjacent an intended site of the lumen, wherein the x-ray catheter comprises a flexible catheter shaft with a distal end and an x-ray generating unit coupled to the distal end. The x-ray generating unit comprises an anode, a cathode and an insulator, wherein the anode and cathode are coupled to the insulator to define a vacuum chamber. The method further comprises causing the emission of an effective dose of x-ray radiation and removing the catheter. The catheter can be inserted after conducting an angioplasty procedure. The catheter can be advanced over a guide wire and through a guide catheter, or through an exchange tube.

DESCRIPTION OF THE FIGURES

FIG. 1A is a cross-sectional view of an x-ray catheter in accordance with a first embodiment of the present invention;

FIG. 1B is a cross-sectional view of a preferred catheter shaft for use in the present invention;

FIG. 14 is a cross-sectional view of a distal portion of a catheter in accordance with the present invention, in a rapid exchange configuration wherein the guide wire passes through the distal tip of the x-ray unit; and FIG. 15 is a partial cross-sectional view of another catheter in accordance with the present invention in a rapid exchange configuration wherein the guide wire enters and exits the catheter shaft proximal to the x-ray unit.

DESCRIPTION OF THE INVENTION

Figure 2A:
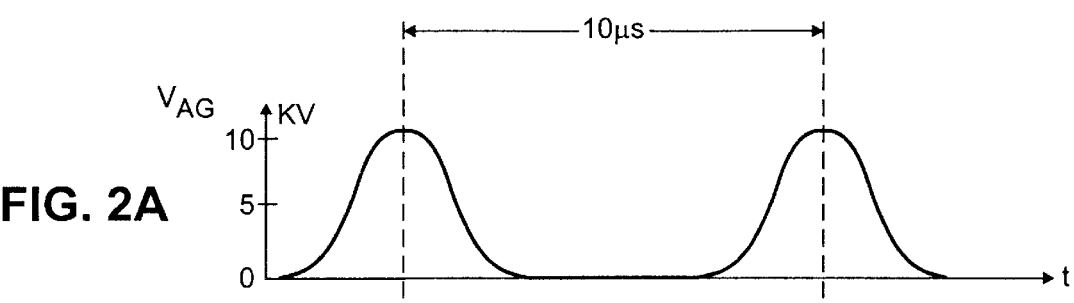
FIG. 2A is a graph of an exemplary voltage applied between the anode and grid electrode versus time.

FIG. 1A is a cross-sectional view of an x-ray catheter 10 in accordance with a first embodiment of the present invention. The x-ray catheter 10 comprises a flexible catheter shaft 12 adapted for insertion into blood vessels or other body vessels. The shaft 12 can be polyethylene, polyurethane, polyether block amide, nylon 12, polyamide, polyamide copolymer, polypropylene, polyester copolymer, polyvinyl difluoride or silicon rubber, for example.

A miniature x-ray unit 14 is secured at the distal end of the catheter shaft 12 by an adhesive, for example. The x-ray unit 14 comprises a vacuum chamber 16, a cathode 18, which emits electrons, and an anode 20, which receives the emitted electrons. The anode 20 abruptly decelerates the impinging electrons, causing the emission of x-ray radiation by the Bremsstrahlung effect, as is known in the art. About 0.1–0.2% of the kinetic energy of the impinging electrons is emitted in the x-ray range of about 0.5–5 Angstroms in the preferred embodiments of the present invention.

In this embodiment, the anode 20 preferably has the shape of an inverted cone. The walls of the anode 20 preferably have an angle of about 16° with respect to the surface of the cathode 18. The anode 20 is preferably a heavy metal, such as gold or tungsten, for example.

The cathode 18 comprises a base 19 which in this embodiment is preferably a ferroelectric material, as discussed below. The base 19 can also be doped or undoped silicon, or other such materials, which is also discussed below.

A grid electrode 24 is coupled to the surface of the base 19 facing the anode 20. A rear electrode 27 is coupled to the rear of the base 19. Wires 26, 28 and 30 extend from the rear electrode 27, anode 20 and the grid 24, respectively, through the catheter shaft 12, to a high voltage generator 32. The generator 32 preferably operates in the 0–30 kilovolt (Kv) range. The wires 26, 28 and 30 can be soldered in place.

Separate lumens 34, 36, 38 can be provided through the catheter shaft 12 for each wire or a single lumen can be provided for a coaxial cable comprising the three wires. A coaxial cable can form the catheter shaft as well, as in the embodiments of FIGS. 5 and 7.

The vacuum chamber 16 preferably comprises a wall 22 of beryllium, beryllium oxide, aluminum, aluminum oxide, pyrolytic boron nitride, graphite or other such metal or ceramic materials, which is transparent to x-rays. If a metal, such as beryllium or aluminum is used as the wall 22 of the vacuum chamber 16, an insulative layer (not shown) would be provided to electrically insulate the anode 20 and cathode 18, as is known in the art. Aluminum oxide, pyrolytic boron nitride and other ceramics are insulators. A transparent biocompatible coating 25 of a polymeric material such as polyethylene, polyurethane or Teflon (R), for example, is also provided over the wall 22. A vacuum tie off (not shown) depends from the vacuum chamber 16, which is sealed after the desired vacuum within the chamber is achieved. A soft, resilient material 48 may be provided at the distal tip of the x-ray unit 14, as is known in the art. The material can be ultra low density polyethylene or nylon, for example.

A lumen 40 extending longitudinally through the catheter shaft 12 can also be provided to accommodate a guide wire 42. A port 44 can be provided through the shaft 12 for the guide wire 42 to exit the shaft 12. A tube 48 can be attached by adhesive or thermal bonding to the shaft 12 at the port 44 to provide a guide for the guide wire 42 around the x-ray unit 14. The tube 48 may be adhered to the wall of the x-ray unit 14, as well. The tube 48 may extend through the soft material 46 at the distal tip of the x-ray unit 14.

The lumens in FIG. 1 are shown in the same plane for illustrative purposes. If multiple lumens are provided, they would preferably be arranged symmetrically within the catheter, as shown in FIG. 1B.

In this embodiment, the base 19 of the cathode 18 is preferably a ferroelectric material, as described in Riege, H., "Electron emission from ferroelectrics—a review," Nuclear Instruments and Methods in Physics Research A340 (1994), pp. 80–89; Gundel, H., et al., "Fast Polarization Changes in Ferroelectrics and Their Application," Nuclear Instruments and Methods in Physics Research A280 (1989), pp. 1–6; Gundel, H., et al., "Time-dependent electron emission from ferroelectrics by external pulsed electric fields," J. Appl. Phys. 69(2) Jan. 15, 1991, pp. 975–982; and Asano, Jun-ichi, et al., "Field-Excited Electron Emission from Ferroelectric Ceramic in Vacuum," Jpn. J. Appl. Phys. Vol. 31 (1992)., pp. 3098–3101, Part 1, No. 9B, which are all incorporated by reference herein. As described in those articles, ferroelectric materials, such as lead-zirconiumtitanate (PZT) and lead-lanthanum-zirconium-titanate (PLZT) and triglycinesulfate (TGS), for example, emit electrons from their surfaces when the spontaneous ferroelectric polarization of these materials is rapidly reversed. High voltage, submicrosecond pulses can cause such reversals, as can mechanical pressure pulses, thermal heating or laser illumination. The use of a laser to cause polarization reversal is discussed in Geissler, K., et al., "Intense laser-induced self-emission of electrons from ferroelectrics," Physics Letters A 176 (1993), pp. 387–392, North Holland, which is also incorporated by reference herein. Ferroelectric cathodes do not require as high vacuum as other types of cathodes. A vacuum of about $10^{-3}$–$10^{-4}$ Torr is sufficient. Ferroelectric cathodes are also simple to manufacture and are reliable.

Preferably, the polarization switching is caused by applying an electrical pulse across the ferroelectric material. Preferably, voltage pulses are applied between the rear electrode 27 and the grid electrode 24. Positive or negative pulses, or a combination of positive and negative pulses, can be used, depending on the configuration and original orientation of the polarization of the ferroelectric material. The reversal of ferroelectric polarization can be achieved by applying a voltage pulse of between about 1–3 Kv to the ferroelectric cathode 18 via the rear electrode 27 and the grid electrode 24. The pulses are preferably applied for 5–100 nanoseconds. The polarization of the ferroelectric material 19 can be switched at a rate of between about 1 kHz–5 MHz. Electrical current densities as high as 100 Amps per square centimeter can be generated. With a polarization switching rate of about 100 kHz, for example, and a diameter of ferroelectric material 19 of about 1 mm, an average anode current of about 10 milliamperes can be generated.

Preferably, a constant voltage or voltage pulses are applied between the anode and the cathode, as well, to control the energy of the emitted x-ray radiation, and hence the depth of penetration of the radiation into tissue. A voltage of about 10–30 Kv is preferred in coronary applications, as discussed further, below.

In this embodiment, the grid electrode 24 is preferably silver, aluminum or gold. About one-half of its area is transparent or open to electrons. The grid 24 can be deposited on a layer of ferroelectric material, such as PZT, PLZT or TGS,; as is known in the art. The dimensions of the cathode 18 depend on the application. For use in coronary arteries, for example, the ferroelectric material 19 can have a diameter of about 1–2 mm. For use in larger blood vessels, such as the femoral artery, the diameter of the ferroelectric material 19 could be up to 3 mm. The thickness of the ferroelectric material 19 can be between about 50–1,000 microns. About 200–500 microns is preferred. The grid 24 is preferably about 0.5–10 microns thick, with about the same diameter as the ferroelectric material 19. The electrode 27 is about 1 micron thick. The distance between the anode 20 and cathode can be about 0.2–5 mm.

Experimental data suggests that restenosis after PTCA can be limited by irradiation by about 2000 centigrays (cGy). (See, for example, Tim A. Fischel et al., "Low-Dose, beta-particle emission from "stent" wire results in complete, localized inhibition of smooth muscle cell proliferation," Circulation, Vol. 90, No. 6, December 1994, and Wiedermann, Joseph G., et al., "Intracoronary Irradiation Markedly Reduces Neointimal Proliferation After Balloon Angioplasts in Swine: Persistent Benefit at 6-Month Follow-Up," JACC Vol. 25, No. 6, May 1995, 1451–6, which are incorporated by reference, herein).

It is believed that the x-ray unit in accordance with this and the other embodiments of the present invention disclosed herein can emit over 2000 centigrays of x-ray radiation in about one minute, to a cylindrical region of a lumen with a length of about 5 mm. Treatment of a typical lesion in a coronary artery, which can be 1–2 centimeters long, can require repositioning of x-ray unit several times to irradiate the entire lesion. A lesion 1–2 centimeters long can therefore be irradiated in about 2–5 minutes. The x-ray catheter of the present invention can deliver sufficient x-ray radiation to a lesion in a short period of time which minimizes the inconvenience and discomfort of the patient and cost of the procedure.

Figure 2B:
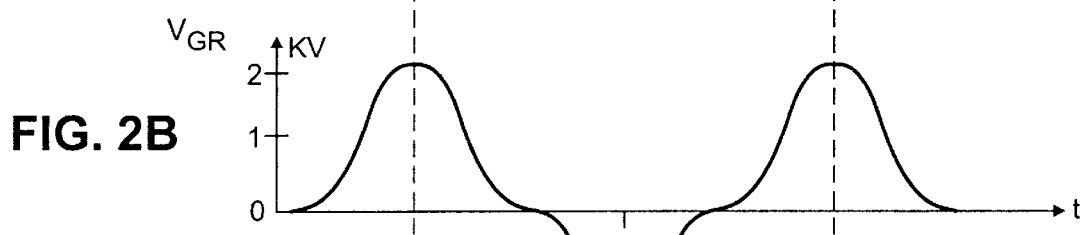
FIG. 2B is a graph of an exemplary voltage applied between the grid electrode and rear electrode of the cathode versus time.
Figure 2C:
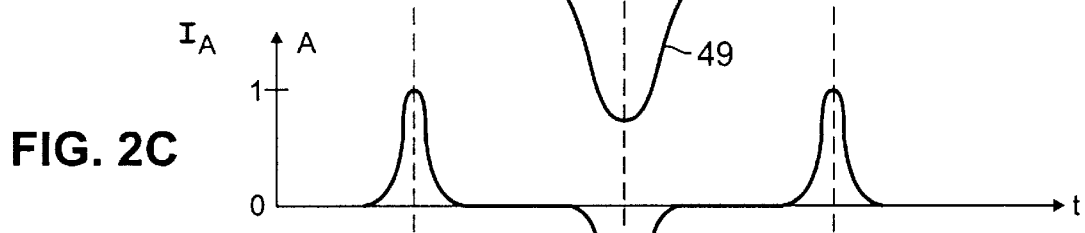
FIG. 2C is a graph of the current flow from the cathode to the anode versus time, for the voltages of FIGS. 2A and 2B.
Figure 2D:
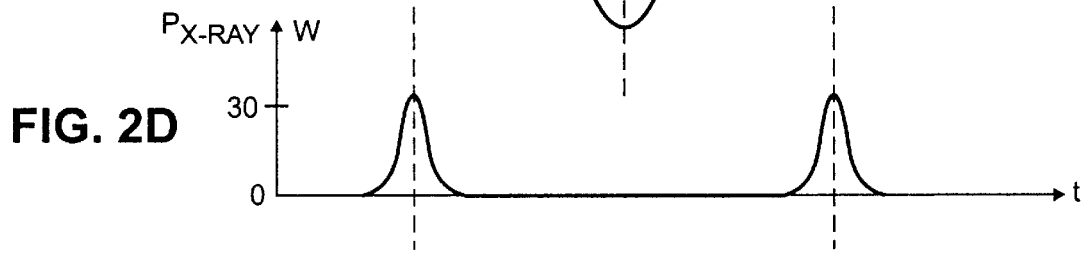
FIG. 2D is a graph of the power of the emitted x-ray radiation for the voltages of FIGS. 2A and 2B.

In operation, the high voltage generator 32 preferably applies voltage pulses between the anode 20 and grid 24, and between the rear electrode 27 and grid, 24. In FIG. 2A, exemplary voltage pulses applied between the anode 20 and grid 24, $V_{AG}$, are plotted versus time. The voltage pulses in this example are about 10–12 Kv. The voltage pulses between the anode 20 and grid 24 can be applied for about 0.1–1.0 microseconds, every 10 microseconds. FIG. 2B plots exemplary voltage pulses $V_{GR}$, applied between the grid electrode 24 and the rear electrode 27 versus time. The voltage difference here is about 2.0 Kv. FIG. 2B also shows a negative pulse 49 which is preferably applied to restore the negative charge on the surface of the ferroelectric material 19 adjacent the grid 24. FIG. 2C illustrates qualitatively the current $I_A$ flowing from the ferroelectric material 19 to the anode 20 for the voltage pulses shown in FIGS. 2A and 2B. The length of each current pulse generated for the range of voltage pulses of 0.1–1 microsecond, is about 10–100 nanoseconds. The current pulses cause the emission of pulses of x-ray radiation with peak power in this example of up to about 30 watts, as shown in FIG. 2D.

Figure 3A:
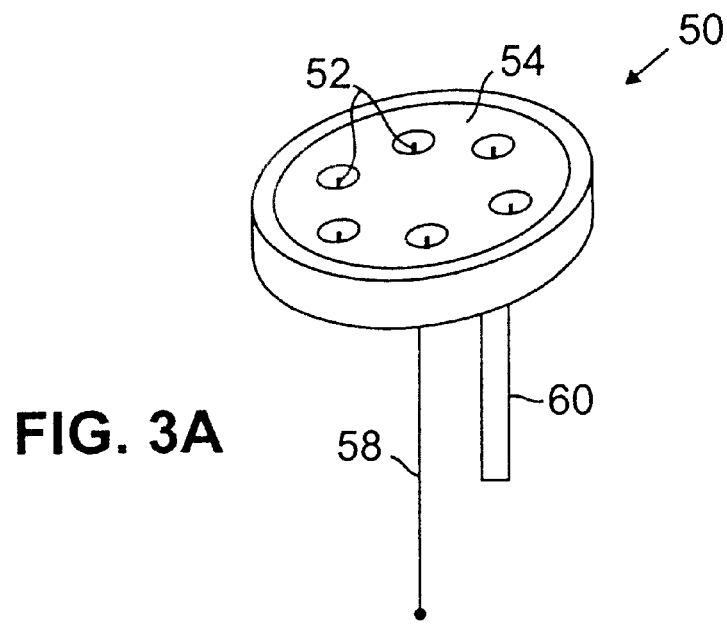
FIG. 3A is an alternative cathode in accordance with a second embodiment of the invention.
Figure 3B:
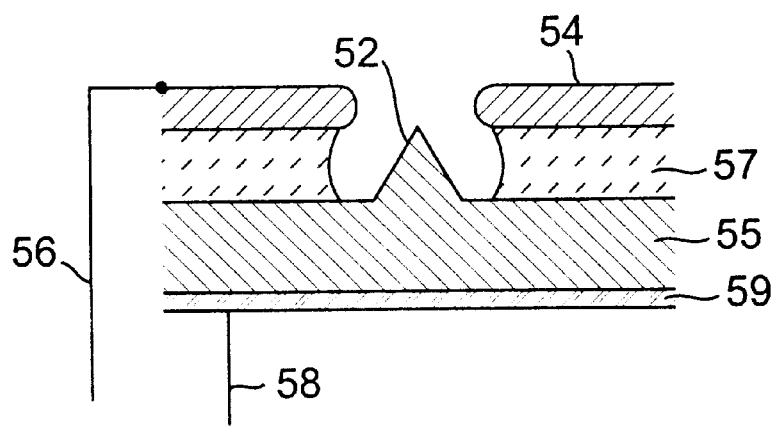
FIG. 3B is an enlarged cross-section of one needle of FIG. 3A.

In a second embodiment of the invention, shown in FIG. 3A, the cathode 18 may also be a field emission cathode 50 comprising multiple needles 52 and optionally a grid electrode 54. FIG. 3B is an enlarged cross-sectional view of a single needle 52, of FIG. 3A. The base 55 and needles 52 can be doped or undoped silicon. The grid 54 can be niobium. If a grid 54 is provided, a layer 57 of an insulator, such as silicon dioxide ($SiO_2$), is preferably deposited over the base 55 of silicon. The grid 54 of niobium is deposited over the silicon dioxide layer 57. A rear electrode 59 is coupled to the rear of the base 55. A wire 58 is coupled to the rear electrode 59. A wire 56 is coupled to the grid 54. Returning to FIG. 3A, a vacuum tie-off 60 is shown, as well. The anode 20 can be the same as described above.

The radius of the tips of the needles. 52 is between about 5–100 Angstroms. The height of the needles is about 0.5–1.0 microns. The grid 54, which is about 0.5 microns thick, is preferably positioned slightly above the top of the needle 52, as shown in FIG. 3B. The openings in the grid 54 have a diameter of about 2 microns. The layer of silicon dioxide is about 1–2 microns thick. A vacuum of between about $10^{-7}$–$10^{-8}$ Torr is preferred for a field emitting cathode including silicon.

The needles 52 emit electrons when negative potential is applied between the rear electrode 59 and the grid electrode 54. A triggering voltage of about 100–500 volts may be used, for example. The voltage can be constant or pulsed. If no grid electrode is provided, the high voltage can be provided directly between the anode and the needles 52.

Figure 4:
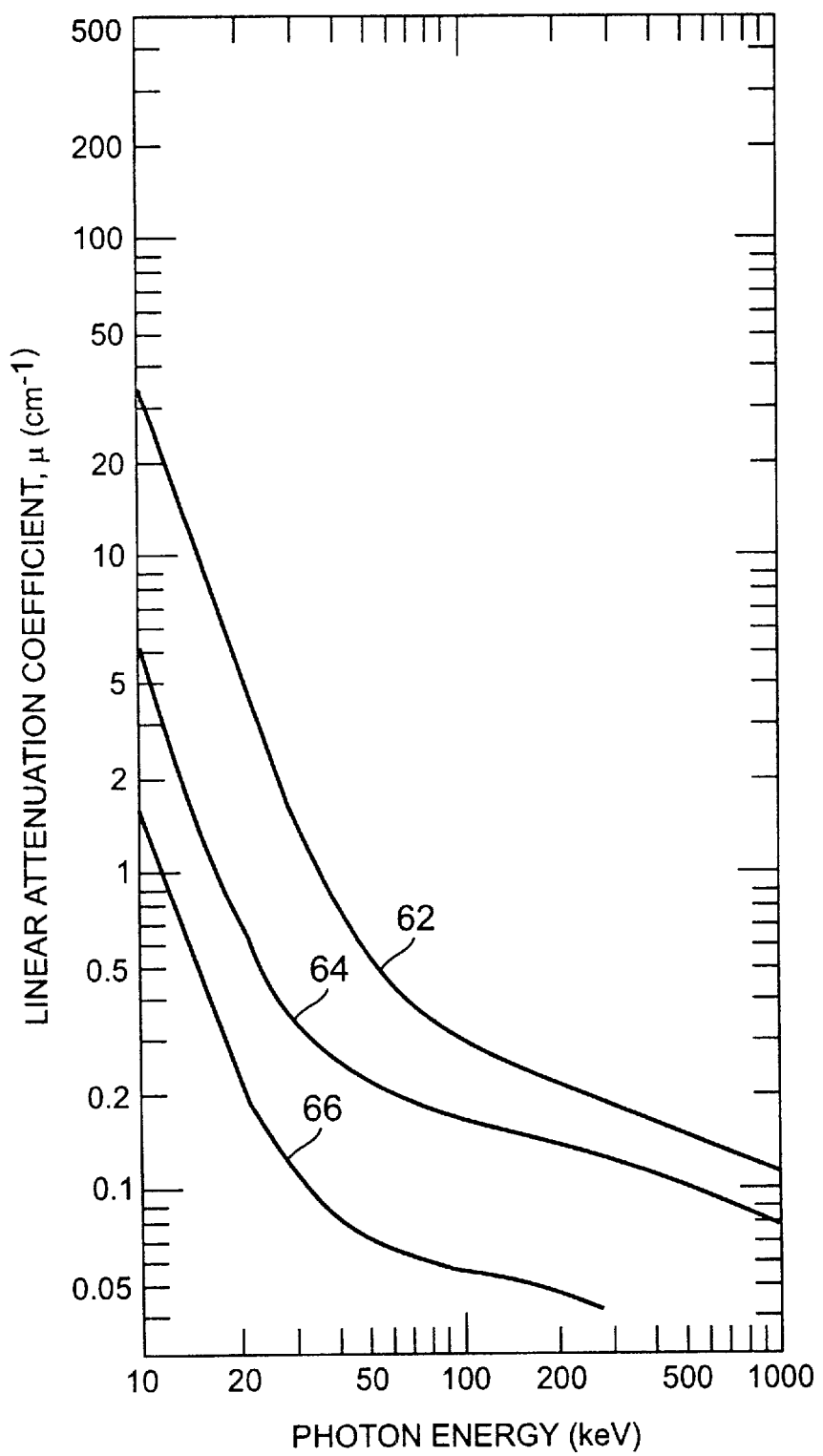
FIG. 4 is a graph of photon energy versus the Linear Attenuation. Coefficient, $\mu$.

The radiation emitted by the anode 18 passes through the vacuum chamber wall 22 and coating 25, into surrounding tissue. Irradiation reduces the ability of smooth muscle cell to proliferate, inhibiting restenosis, as discussed above. FIG. 4 is a graph of Photon Energy (kev) versus the Linear Attenuation Coefficient $\mu$ ($cm^{-1}$) for bone 62, muscle 64 and lung tissue 66. (See, Anthony Brinton Wolbarst, Physics of Radiology, Appleton and Lange, 1993, p. 108; Johns, H. E., Cunningham, J R.: The Physics of Radiology, 4th ed., Springfield, Ill.; Charles C. Thomas, 1983, Appendix A.) The greater the coefficient $\mu$, the more effectively the medium absorbs and scatters photons. The depth of penetration of radiation is the depth at which the intensity of the impinging radiation drops to 1/e of its original value. The depth of penetration of x-ray radiation of a particular energy is equal to $1/\mu$. Generally, the coefficient $\mu$ increases with increasing effective atomic number of the material. While muscle and lung tissue have nearly identical chemical composition, the attenuation in muscle tissue is about 3 times greater than the attenuation in lung tissue, because muscle tissue is about 3 times denser than lung tissue. The energy of x-ray radiation is preferably adjusted so that it penetrates slightly into the adventitia tissue of the blood vessel about 2 mm deep. Penetration into the cardiac muscle tissue beyond the coronary artery, for example, should be minimized. The energy can be adjusted by varying the voltage applied between the anode and cathode. The preferred voltage range of 10–30 Kv yields x-ray radiation with a peak energy of about 8–10 KeV, which is appropriate in coronary applications.

Figure 5:
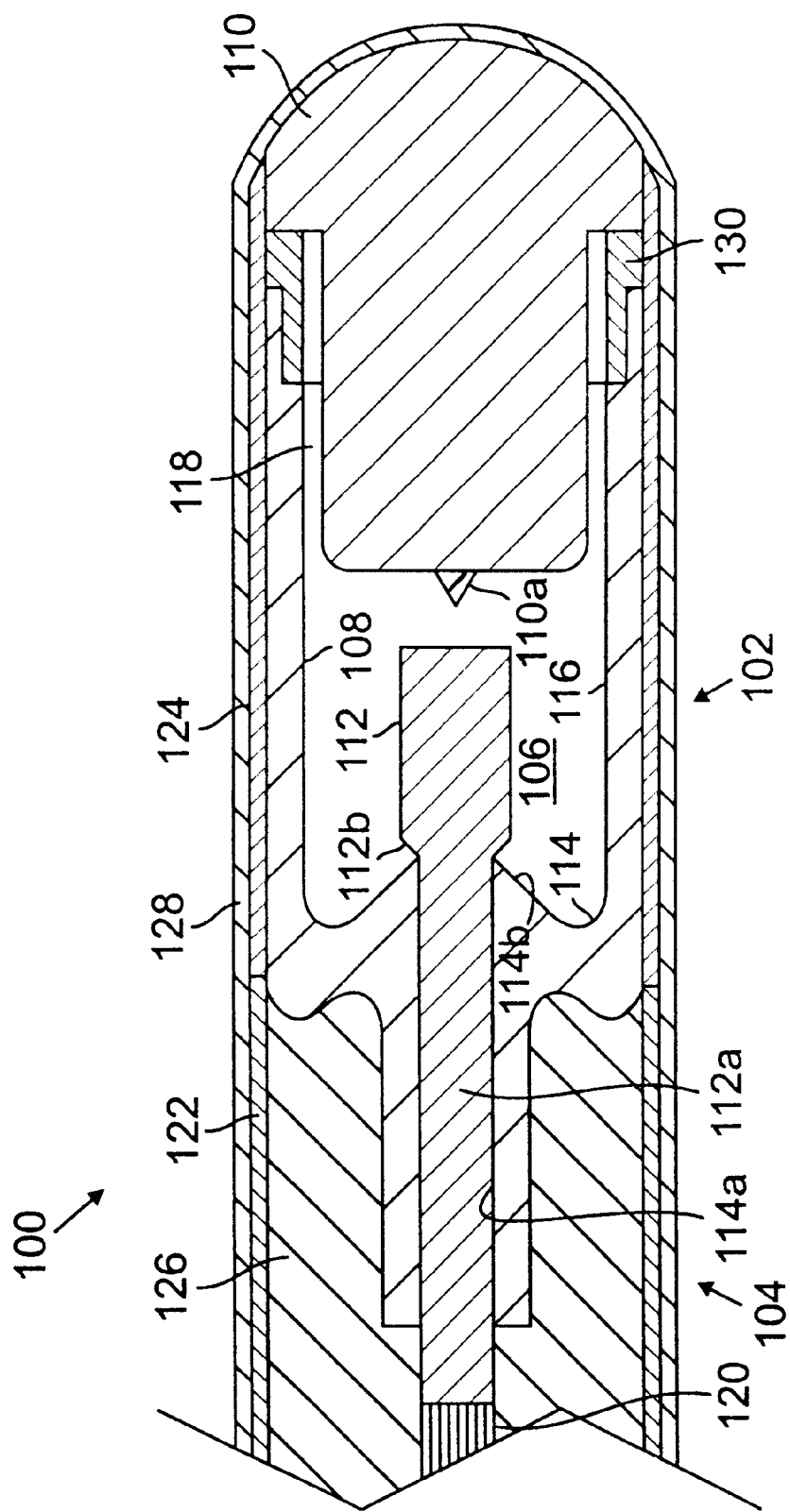
FIG. 5 is a cross-sectional view of the distal portion of a third embodiment of the present invention.

FIG. 5 is a cross-sectional view of the distal portion of an x-ray catheter 100 in accordance with a third embodiment of the present invention. The x-ray catheter 100 comprises an x-ray unit 102 coupled to a high voltage coaxial cable 104. The x-ray unit 102 has a vacuum chamber 106, defined by an insulator 108, a cathode 110 and an anode 112. The insulator 108 comprises a base portion 114 coupled to a tubular, preferably cylindrical wall portion 116 with an open end 118. The cathode 110, which is a cold, field emission cathode, is coupled to the open end 118. The insulator 108 is preferably alumina, beryllium oxide or more preferably, pyrolytic boron nitride. The boron nitride must be pyrolytic, as opposed to sintered, because only the pyrolytic boron nitride is vacuum tight at the wall thicknesses required. The cathode 110 is preferably graphite. The anode 112 is preferably tungsten or tungsten coated with a layer of platinum. A one micron layer of platinum is sufficient. The vacuum is preferably $10^{-5}$ Torr or better.

The cathode 110 is preferably graphite, carbides, such as titanium carbide, silicone, metals, or graphite coated with titanium carbide. The cathode 110 preferably includes one or a plurality of protrusions 110a with a sharp tip extending towards the anode 112 along a central axis of the x-ray unit 102. The protrusion 110a locally enhances the electrical field and improves the emission of electrons, as is known in the art. The protrusion 110a can comprise the same material as the cathode 110, or can be another of the cathode materials mentioned above.

The anode 112, which is preferably in the shape of a rod, extends along the central axis of the x-ray unit 102. The rod 112 has a depending portion 112a received within a cylindrical groove 114a extending through the base portion 114. Preferably, the base 114 has a portion 114b, which tapers toward the anode 112. An angle of about 45° can be used, for example. The anode 112 also can have a portion 112b tapered toward the cylindrical portion 114b of the base. Such a configuration displaces the electrical field from the anode-vacuum-insulator triple junction, decreasing the risk of electrical flashover during operation. The anode 112 is preferably a heavy metal. Tungsten is preferred.

The cathode 110 and anode 114 are coupled to the high voltage generator 32 of FIG. 1, described above, through the high voltage coaxial cable 104. The coaxial cable 104 comprises a central conductor 120, which is coupled to a proximal end of the anode 114, and an external conductor 122, which is coupled to the cathode 110. A conductive coating 124 is provided over the external surface of a portion of the cathode 110 and the external surface of the insulator 108 to couple the cathode 110 to the external conductor 122. A silver coating with a thickness of about 0.1–1.0 microns may be used. Gold may be used as well. Insulation 126, such as Teflon (R), silicone, rubber, fluorinated ethylene propylene (FEP) or polyethylene, for example, is typically provided between the external conductor 122 and the central conductor 120. The x-ray unit 102 can be attached to the coaxial cable 114 with an adhesive, for example.

The cathode's "triple junction point" (the junction between the cathode, the insulator and the vacuum), which in this embodiment is an annular region surrounding the cathode 110 proximate the open end 118 of the insulator 108, is screened from the high electrical field between the anode 112 and the cathode 110 by the conductive coating 124 and the side of the cathode 110. This decreases the incidence of electrical flashover, enabling the use of higher voltages.

The cathode 110 can be coupled to the open end 118 of the insulator 108 through a metal ring 130. The metal ring can comprise tungsten, platinum, or graphite covered by platinum. Coupling of the cathode 110 to the metal ring and coupling of the anode 112 to the insulator 108 is described further, below.

A biocompatible layer 128 is provided over the external conductor 116, conductive layer 124, and the cathode 110. A thickness of less than about 0.002 inches is preferred. Preferably, the biocompatible coating 128 also acts as an insulating layer. The biocompatible coating may be silicone or FEP, for example. A lubricious layer (not shown) of a hyaluronic coating, for example, may be provided as well. The biocompatible coating may have sufficient lubricity without a further coating. Silicone, for example, is a highly lubricious biocompatible coating.

The coaxial cable 104 is chosen to have sufficient flexibility to be advanced through the cardiovascular or other such system, to an intended site. It has been found that standard high voltage coaxial cables are generally not flexible enough to be advanced through the cardiovascular system to the coronary arteries. It has further been found, however, that miniature high frequency coaxial cables are available with sufficiently small diameter (about 1.0–3.0 mm outer diameter) and sufficient flexibility to be advanced to the coronary arteries. Usually, such cables are used in high frequency applications at voltages less than several kilovolts. Surprisingly, it has been found in connection with the present invention that these cables can hold direct current voltages as high as 75–100 Kv without breakdown, and consequently can be used with the x-ray unit of the present invention for operational voltages of up to 30–40 Kv. Such voltages are sufficient to generate x-ray radiation in appropriate energy ranges for the treatment of restenosis and other conditions. Suitable coaxial cables include CW2040-3050FR; CW2040-30; CW2040-3675-SR; and CW2040-3275SR, distributed by Cooner Wire, Inc. Chatsworth, Calif., for example. Cooner distributes coaxial cables for New England Electric Wire Corporation,. Lisborn, N.H.

An x-ray unit 102 in accordance with this embodiment of the invention can have a length less than about 15 mm and a diameter less than about 4.0 mm, depending on the application. The distance between the cathode 108 and the anode 110 can be between about 2:0–0.2 mm, depending on the size of the x-ray unit 102. The thickness of the cylindrical insulator wall 116 can be between about 0.2–0.5 mm. The diameter of the coaxial cable 104 can be about the same as the diameter of the x-ray unit 102. For use in preventing restenosis after dilatation of a coronary artery, which typically has a diameter of about 3 mm, the x-ray unit 102 preferably has a length of about 7 mm and a diameter of about 1.5 mm. In peripheral blood vessels, which are larger, the x-ray unit 102 preferably has a diameter of about 3.5 mm and a length of between about 7–15 mm. Larger x-ray units with greater diameters and lengths than those discussed above could also be made and used in accordance with the present invention.

To operate the x-ray unit 101 to prevent restenosis in a vessel of the cardiovascular system, for example, direct current having a voltage of between about 10–30 Kv, can be applied to the central conductor 120. The external conductor is connected to ground. Electrons emitted from the cathode 110 due to a field emission effect impact the anode 112, causing the emission of x-ray radiation of about 8–10 KeV, as discussed above. The radiation is primarily emitted radially, to the vessel wall. About 10–30 Kv is preferred for use in the prevention of restenosis. Higher voltages will cause the emission of x-ray radiation of higher energy which can penetrate too deeply into the vessel wall, damaging cardiac tissue. Higher voltages may be used for other applications.

Voltages at the higher end of the 10–30 Kv range are preferred because the use of higher voltages enables the generation of the same amount of radiation with less current than the use of a lower voltages, and is therefore more efficient. Higher voltages also enable the generation of x-ray radiation of higher power. Higher power, however, can cause the generation of more heat, which can damage the tissue of a vessel wall. In this embodiment, most of the heat is generated at the anode 110 positioned at the center of the x-ray unit, as far from the vessel wall as possible.

Higher voltage also increases the risk of electrical flashover at the anode and cathode triple junctions. As discussed above, the anode 112 and cathode 110 are preferably configured to minimize the risk of flashover.

Bulk electrical breakdown is also a risk with increased voltages. Pyrolytic boron nitride has a high dielectric strength, enabling the x-ray unit of the catheter to tolerate the voltages used in this application without bulk electrical breakdown. The dielectric strength of pyrolytic boron nitride is 200–600 KV/mm.

Pyrolytic boron nitride is also particularly preferred as the insulator 108 because it is highly transparent to soft x-rays and can therefore be efficiently used as an x-ray window. The coefficient of linear absorption of boron nitride at about 8 Kev, the average energy of the emitted radiation, is 1.0 mm$^{-1}$. About 8–10 KeV is the preferred energy level of x-ray radiation in the treatment of restenosis, as discussed above. Transmission of radiation through pyrolytic boron nitride with a thickness of about 0.3 mm is about 70%. This enables irradiation of tissue at a rate of at least about 1 gray per minute. Preferably, about 10–30 grays per minute of radiation at about 8–10 KeV are provided, enabling delivery of an effective amount of radiation to prevent restenosis to a lesion about 5 mm long in about 1 minute. It is believed that x-ray radiation can be delivered at a rate of over 50 grays per minute with the x-ray unit of this embodiment. A lesion 1–2 cm long can be treated in about 2–5 minutes by progressively repositioning the x-ray unit to irradiate additional portions of the lesion.

Positive electrical pulses with a peak voltage of between about 15–30 Kv and 2–100 nanoseconds long can also be applied to the central conductor 120 of the coaxial cable 104 at a rate of between about 1–50 KHz. The high voltage pulses cause field emission. The pulses can further cause a vacuum electrical breakdown, causing electrons to flow from the cathode 110 to the anode 112 through a plasma of vaporized cathode and anode material between the cathode 110 and the anode 112.

The anode 114 is preferably attached to the insulator 108 of pyrolytic boron nitride during formation of the insulator 108 by chemical vapor deposition (CVD). During CVD, the deposited boron nitride chemically bonds to the anode material, forming a strong, vacuum tight seal. The seal formed by CVD has higher voltage hold-off because it does not have voids which can locally enhance the electrical field and cause electrical flashover.

Figure 6:
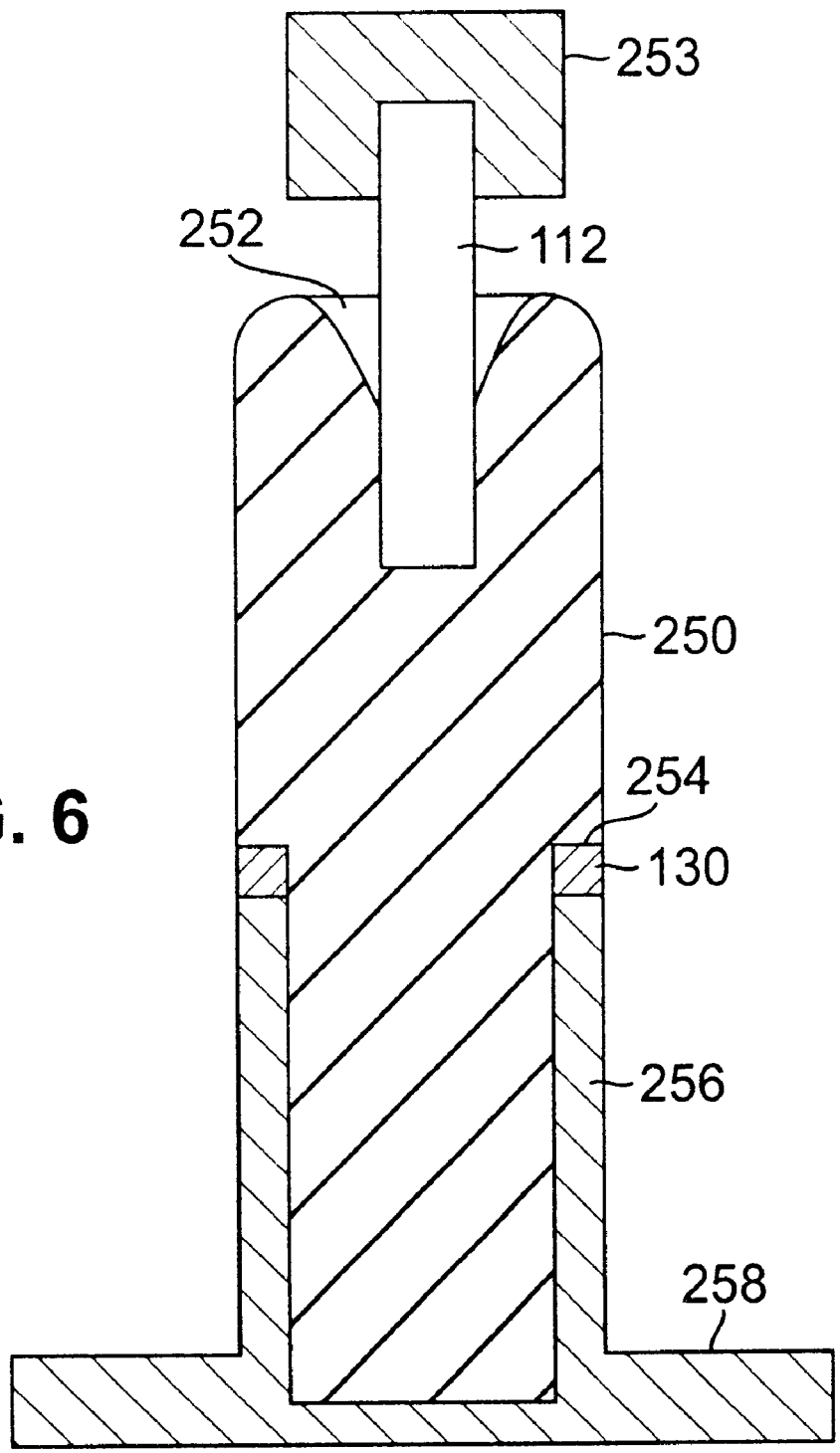
FIG. 6 is a cross-sectional view of mandrel for use in chemical vapor deposition of the insulator of the embodiment of FIG. 5.

A mandrel 250 for use in manufacturing the x-ray unit 102 by CVD is shown in FIG. 6. The mandrel 250 is preferably graphite. A cavity 252 is provided in the mandrel 250 for receiving the anode 114. The anode 114 is secured in an anode holder 254 of boron nitride, for example. The mandrel 250 includes a shoulder 254 for supporting the metal ring 130. The metal ring 210 is held in place by a cylindrical ring holder 256, also of boron nitride, for example, which is supported by a mandrel holder 258 of graphite, for example.

The assembly of FIG. 6 is placed in a CVD reactor for the deposition of boron nitride by CVD, as is known in the art. Chemical vapor deposition of boron nitride is described, for example, in Matsuda, et al., "Synthesis and Structure of Chemically Vapour-Deposited Boron Nitride," Journal of Materials Science 21 (1986) pp. 649–658; and Pouch, John J., et al. "Synthesis Properties of Boron Nitride," Materials Science Forum, Volumes 54 and 55 (1990) pp. 141–152, for example, which are incorporated by reference, herein. The boron nitride is deposited on the hot surface of the assembly, crystallizing into a hexagonal structure. CVD of pyrolytic boron nitride can be performed by CVD Products Incorporated, of Hudson, N.H., for example.

It may be advantageous to deposit and impregnate boron onto the surface of the graphite mandrel 250 and tungsten anode 114 prior to depositing the boron nitride. To increase the chemical stability of the anode 114 during the deposition procedure, the tungsten could be coated with a layer of platinum about 1 micron thick.

After completion of the CVD process, the mandrel 250 is removed from the assembly by oxidation of the graphite, also as known in the art.

The cathode 110 is then vacuum brazed to the metal ring 130 with brazing materials, which are discussed below, sealing the chamber. Vacuum brazing is also known in the art and can be provided by Koral Labs., Minneapolis, St. Paul, for example. The sealed chamber is then covered with the conductive coating 124 by metal vapor deposition, for example.

Such a process can be used for mass production of large numbers of assemblies.

Figure 7:
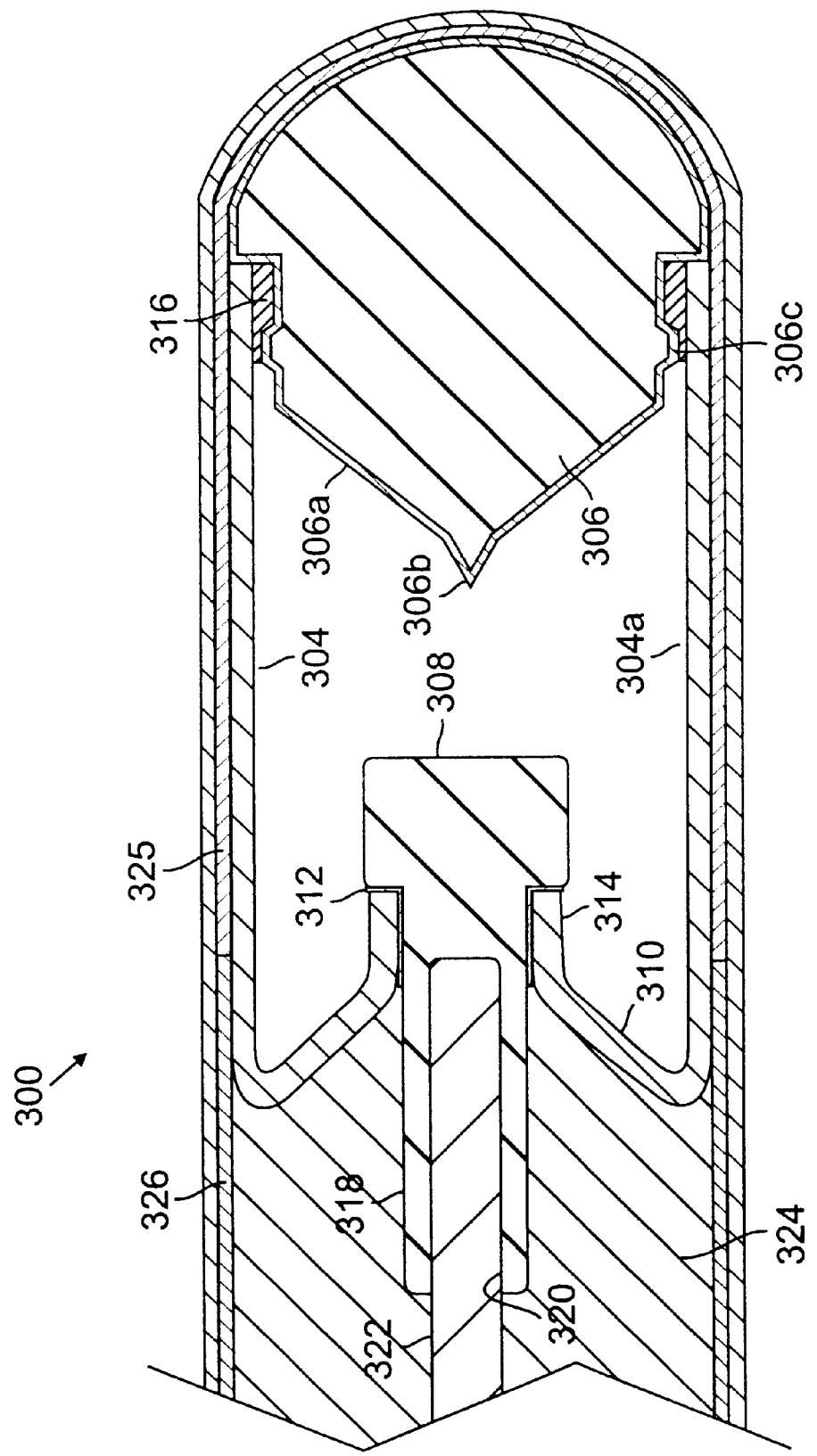
FIG. 7 is a cross-sectional view of the distal portion of a fourth embodiment of the present invention.

A fourth embodiment of an x-ray unit 300 in accordance with the present invention is shown in FIG. 7. The x-ray unit 300 comprises a vacuum chamber 302 defined by an insulator 304, preferably of pyrolytic boron nitride, a cathode 306, and an anode 308. The anode 308 is preferably tungsten.

The cathode 306 may be graphite, titanium carbide, graphite coated with titanium carbide or stainless steel, for example. Graphite coated with titanium carbide is preferred. A coating of severalmicrons may be used. Titanium coating can be provided by Lanxide Coated Products, Inc., Newark, Del., for example. The cathode 306 preferably includes an annular protrusion 306c for creating a cavity for containing the brazing material 316. The cathode 306 may also include a protrusion 306a directed towards the anode 308, as in the embodiment of FIG. 5.

The insulator 304 comprises a cylindrical wall 304a with an inclined depending wall 310 and a cylindrical wall 314 preferably parallel to the cylindrical wall 304a. The depending wall 310 is preferably angled towards the interior of the vacuum chamber 302. The cylindrical wall 314 defines a sleeve for receiving a depending portion 318 of the anode 308. The anode 308 is coupled to the cylindrical wall 314 through a brazing alloy 312. The cathode 306 is coupled to the open end 314 of the insulator 304 through a brazing alloy 316, as well.

The depending portion 318 of the anode 308 preferably includes a slot 320 for receiving the central conductor 322 of a coaxial cable 324. The cathode 306 is coupled to the external conductor 326 of the coaxial cable 324 through a conductive layer 325, as in the embodiment of FIG. 5. A biocompatible coating is also provided over the coaxial cable 324, conductive layer 325 and cathode 306. A lubricious coating (not shown) may be provided, as well.

Preformed pyrolytic boron nitride of the desired sizes and shapes is available from CVD Products, Incorporated, for example.

Appropriate brazing alloys for coupling pyrolytic boron nitride to the tungsten anode 308 include Incusil-15 ABA and Incusil-ABA, for example, available from GTE Products Corporation, WESTGO Division, Belmont, Calif. ("WESTGO"). Incusil-15 ABA comprises 14.5% indium, 1.25% titanium, 23.5% copper and 60.75% silver. Incusil-ABA comprises 12.5% indium, 1.25% titanium, 27.5% copper and 59% silver. The brazing temperatures for both alloys is about 750° C. The brazing material can be in the form of a cylindrical ring placed within the sleeve formed by the cylindrical wall 314 in FIG. 7. The brazing material spreads into the vertical region between the anode 308 and wall 314 during the brazing process. These alloys can also be used to braze the cathode 110 to the metal ring 130 in the embodiment of FIG. 5.

Appropriate brazing alloys for coupling a cathode 308 of graphite or graphite coated with titanium carbide to pyrolytic boron nitride include Cusin-1 ABA and Cusil-ABA, also available from WESTGO. Cusin-1 ABA comprises 34.25% copper, 1.75% titanium, 1.0% tin and 63% silver. Cusil-ABA comprises 63% silver, 35.25% copper and 1.75% titanium. The brazing temperatures for both alloys is about 850° C. The brazing is also conducted in a vacuum of about $10^{-5}$ Torr or better. Because it requires a higher brazing temperature, the graphite cathode 306 is coupled to the pyrolytic boron nitride prior to the tungsten anode 308. The brazing material can be in the form of a ring or it can be sputtered onto the end of the pyrolytic boron nitride prior to vacuum brazing.

Figure 8:
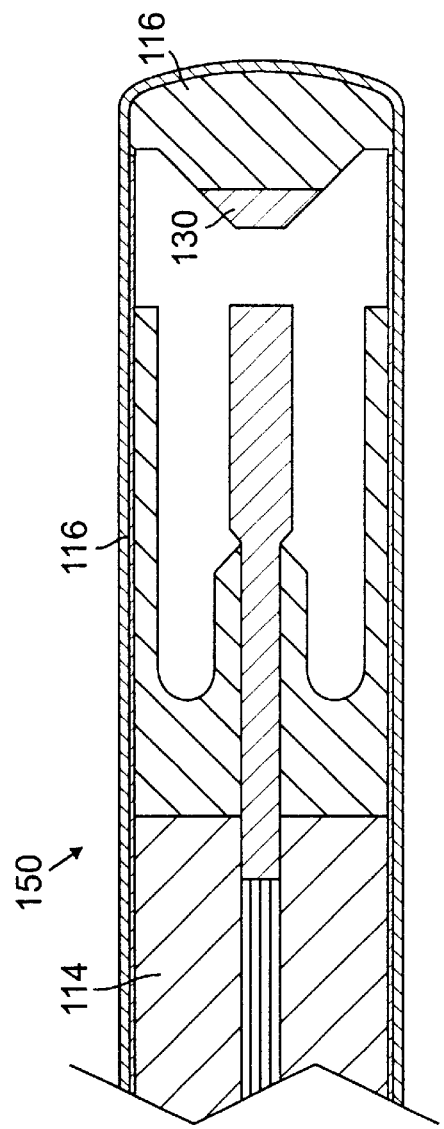
FIG. 8 is a cross-sectional view of the distal portion of a fifth embodiment of the present invention.

Instead of a cathode of graphite, the cathode can be PLZT or other such ferroelectric material, as discussed above. As above, the use of ferroelectric material requires the use of voltage pulses. In FIG. 8, a fifth embodiment of the present invention is shown, comprising a ferroelectric cathode 130 supported by a conductive cap 132. The conductive cap 132 is coupled to the outer conductor 116 of the coaxial cable 114 by a conductive layer 118, as above. The remainder of the x-ray catheter 150 is the same as the embodiment of FIG. 5. Graphite is preferred as the conducting material because it has a low absorption coefficient for x-ray, enabling transmission through the distal end of the x-ray unit.

Figure 9:
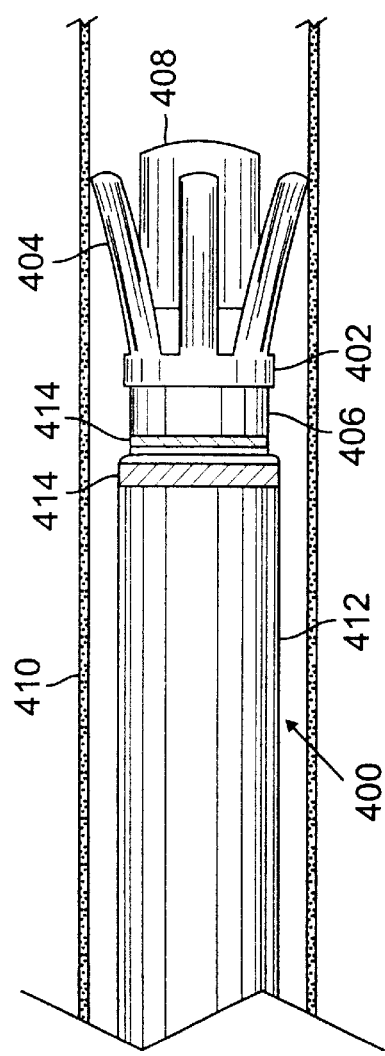
FIGS. 9–11 are side views of the distal portions of the catheter of the present invention, including several centering devices for centering the x-ray unit within a lumen.

It is preferable to center the x-ray unit within the vessel or lumen, to provide a uniform distribution of x-ray radiation around the circumference of the vessel wall. FIG. 9 is a side view of an x-ray catheter 400 in accordance with the present invention, with a centering device comprising a plastic sleeve 402 with a plurality of resilient polymeric solid arms 404 depending from it at an angle. The sleeve 402 can be coupled to the outer, biocompatible layer of the coaxial cable 406 proximal to the x-ray unit 408 by adhesive or thermal bonding, for example. The distal ends of the arms 404 can optionally extend beyond the distal end of the x-ray unit 408. The arms 404 bear against the vessel wall 410, centering the x-ray unit 408 within a vessel or lumen of the body.

A sheath 412 is preferably provided over the coaxial cable 406,for compressing the arms.404 during advancement of the x-ray unit 408 to the intended site. When the x-ray unit 408 is properly positioned, the sheath 410 is retracted, releasing the arms 404. Radiopaque bands 414 of gold or tantalum, for example, are preferably provided on the coaxial cable 406 and the sheath 412 to assist in tracking of the x-ray catheter 400 on a fluoroscope during a procedure. The bands 414 are preferably positioned on the coaxial cable 406 and the sheath 412 such that when the sheath 412 has been sufficiently retracted to release the arms 404, the bands on the coaxial cable 406 and the sheath 412 are essentially aligned.

Figure 10:
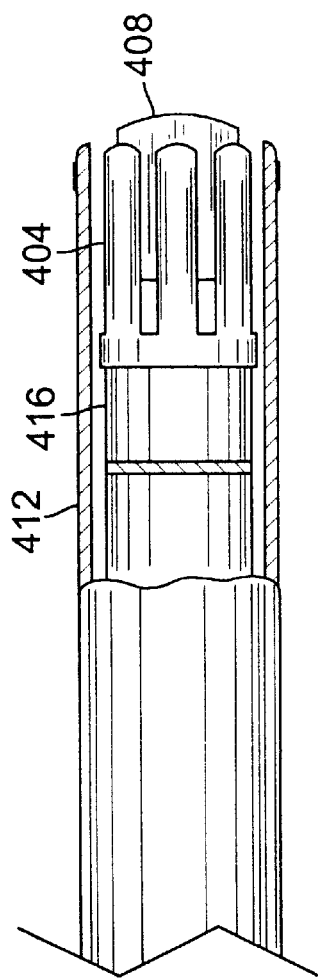

FIG. 10 is a partial, cross-sectional view of the x-ray catheter 400 of FIG. 9, wherein the x-ray unit 408 is within the sheath 412 and the arms 404 are compressed. Saline or some other cooling agent can be delivered through the space 416 between the sheath 412 and the coaxial cable 406, as well.

Figure 11:
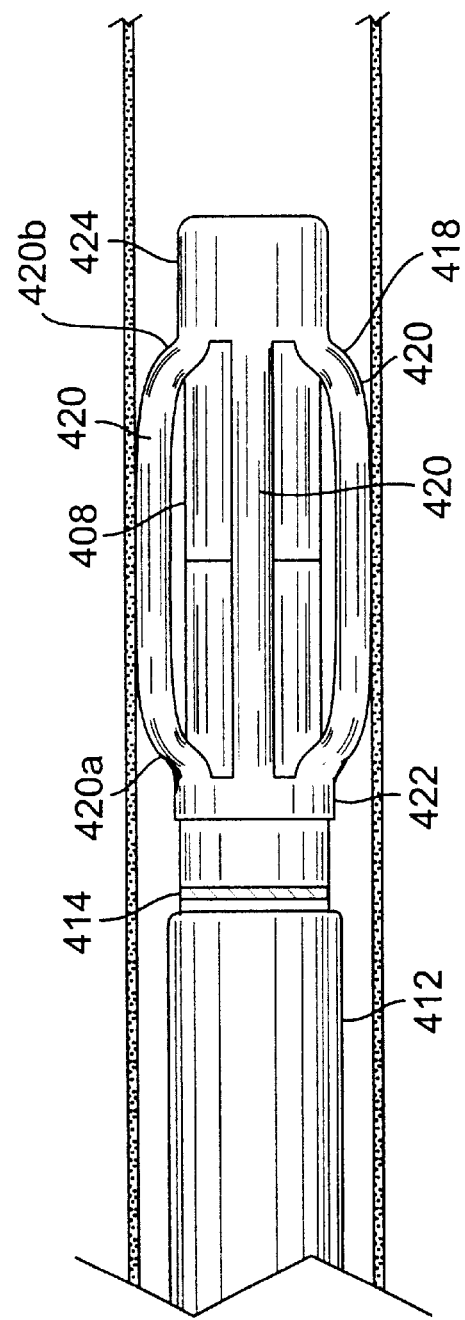

Alternatively, a compressible cage 418 can be provided over the x-ray unit 408 as a centering device, as shown in FIG. 11. The cage 418 comprises a plurality of arms 420 with a first end 420a coupled to a first sleeve portion 422 and a second end 420b coupled to a second sleeve portion 324. The x-ray catheter unit 408 extends into and lies within the region defined by the arms 418. The arms 408 can be compressed by the sheath 412, as in FIG. 14. The second portion 424 can be coupled to the distal end of the x-ray unit 308.

The material of the outer layer of the coaxial cable 406 and the material of the sheath 412 preferably comprise materials which slide easily with respect to each other. The outer layer of the coaxial cable 406 is preferably coated with a lubricious material, such as silicone or a hyalurdnic coating, as well.

Releasable arms and cages, methods of their manufacture and suitable materials are disclosed in U.S. Ser. No. 08/488, 216, filed on Jun. 7, 1995 and assigned to the assignee of the present inventor. U.S. Ser. No. 08/488,216 is incorporated by reference, herein.

Another method of centering the x-ray unit is a malecot device, as shown in FIGS. 12–13. A sheath 450 of plastic material is attached to the distal portion 454a of an x-ray unit 454, which is shown in FIG. 12. The coaxial cable 456 attached to the proximal end of the x-ray unit, is also shown in phantom. A plurality of lateral slots 457 are provided through portions of the sheath surrounding the x-ray unit 454. Four equidistantly positioned slots 457 may be provided around the circumference of the sheath 450, two of which are shown in FIG. 12. The length of the slots 457 depends on the diameter of the vessel at the intended site and the diameter of the sheath 450, and should be sufficient to enable the buckled portion of the sheath 450 to bear against the circumference of the vessel wall. When the x-ray unit 454 is adjacent the intended site, the sheath 450 is advanced, causing a portion 458 of the sheath 450 between the slots 457 to buckle outward, as shown in FIG. 13. The sheath 450 is advanced a sufficient distance for the portion 458 to buckle sufficiently to bear against the vessel wall, centering the x-ray unit 454. The distal tip 460 of the catheter may be of a soft, resilient material such as ultra low density polyethylene or nylon, for example, as is known in the art. Any of the embodiments of the x-ray catheter can be provided with a soft tip.

The x-ray unit could also be placed within an expandable balloon.

The x-ray catheters of the embodiments of FIGS. 5, 7 and 8 can be conveyed to the site of the dilatation procedure through an exchange tube after the dilatation catheter is removed. The exchange tube can be advanced to the intended site over the same guide wire used in the dilatation procedure. After the exchange tube is properly positioned, the x-ray catheters of FIGS. 5, 7 and 8 can be advanced through the exchange tube, to the intended site.

The x-ray catheter of the present invention can also be advanced over the same guide wire used by the dilatation catheter after the dilatation catheter is removed, through a guide catheter. FIG. 1 shows one such x-ray catheter 10. FIG. 14 is a cross-sectional view of another x-ray catheter 500 for use with a guide wire 502 in a rapid exchange configuration. The guide wire 502 enters the x-ray unit 504 through an opening 506 in the cylindrical wall of the unit 404, extends through the center of the unit 504 and a central passage 508 in a cathode 510, exiting through an opening at the distal end of the unit 504.

The cathode 510 of the x-ray unit 504 may be graphite, for example. The anode can comprise a base 514 of tungsten, for example, with a plurality of rod-like protrusions 516 arranged concentrically about the base within a vacuum cavity 518 defined by an insulator 520 and a cathode 510. The protrusions 516 extend toward the cathode 510. The insulator 520 is preferably of pyrolytic boron nitride. A tube 522 of insulative, vacuum tight material, may be provided through the vacuum chamber 518, providing a passage for the guide wire 502.

The base 514 of the anode has a depending portion 514a, preferably coupled to the central electrode 417 of a coaxial cable 518. A conductive layer is provided over the outer walls of the insulator 520, to couple the cathode 510 to the outer electrode of the coaxial cable 518, as described in the embodiments, above.

FIG. 15 is a side view of another embodiment of a rapid exchange x-ray catheter 600 in accordance with the present invention, wherein a portion of the catheter shaft 602 is shown in cross-section. Here, a lumen 601 is provided in the catheter shaft 602 with an entrance port 603 and an exit port 604 proximal to the x-ray unit 605. A guide wire 606 enters the lumen 601 through a port 603 and exits through a port 604. The x-ray catheter 600 can be tracked along the guide wire 606 to the intended site in a lumen or vessel, through the lumen 601. The distance between the entrance port 602 and the exit port 604 can be about 10–20 cm, for example. Other lumens (not shown) can be provided for a coaxial cable or wires to couple the x-ray unit 605 to the high voltage generator 32 shown in FIG. 1, for example.

Such a catheter shaft 602 can be formed in a multi-lumen extrusion process, as is known in the art, wherein the lumens extend longitudinally through the catheter shaft 602. The portions of the lumen distal and proximal to the intended locations of the exit port 604 and entrance port 602 can be closed, as is known in the art. The ports 603, 604 can then be made through the catheter shaft by a laser, for example.

While the above embodiments are described with respect to applying x-ray radiation to the site of an angioplasty procedure, the present invention can be used to apply radiation within the cardiovascular system for other purposes, or to other vessels, lumens, or cavities in the body, wherever the application of radiation would be useful.

The various embodiments set forth above are for the purpose of illustration. It will be appreciated by those skilled in the art that various changes and modifications may be made to these embodiments without departing from the spirit and scope of the invention as defined by the claims, below.

We claim:

1. An x-ray catheter comprising:
a flexible catheter shaft for being advanced through lumens of the vascular system, the catheter shaft having a distal end;
an x-ray unit coupled to the distal end, the x-ray unit comprising an anode, a cathode, an insulator having an external surface, and a conductive coating on the insulator, wherein the anode and cathode are coupled to the insulator to define a vacuum chamber.

2. The catheter of claim 1, wherein the anode comprises tungsten or platinum and the cathode comprises graphite.

3. The catheter of claim 1, wherein the cathode is a field emission cathode.

4. The catheter of claim 1, wherein the x-ray unit irradiates tissue at a rate of at least about 1 gray per minute.

5. The catheter of claim 1, wherein the insulator comprises pyrolytic boron nitride.

6. The catheter of claim 5, wherein the cathode and anode are coupled to a voltage generator.

7. The catheter of claim 6, wherein the catheter shaft comprises a coaxial cable coupling the anode and cathode to the voltage generator.

8. The catheter of claim 7, further comprising means for centering the x-ray unit within a lumen.

9. A catheter for emitting x-ray radiation in a vascular system, the catheter comprising:
a flexible catheter shaft having a distal end;
an x-ray unit coupled to the distal end, wherein the x-ray unit comprises an anode, a cathode, an insulator having an external surface, and a conductive coating on the external surface of the insulator, wherein the anode and cathode are coupled to the insulator to define a vacuum chamber and the conductive coating is electrically connected to the cathode.

10. The catheter of claim 9, wherein the insulator is chosen from the group consisting of beryllium oxide, aluminum oxide, or pyrolytic boron nitride.

11. The catheter of claim 9, wherein the cathode and the anode are coupled to a voltage generator.

12. The catheter of claim 9, further comprising a means for centering the x-ray unit within a lumen.

13. The catheter of claim 9, wherein the cathode is a ferroelectric material.

14. The catheter of claim 9, further comprising a guide wire lumen.

15. The catheter of claim 14, wherein the guide wire lumen extends partially through the catheter shaft.

16. The catheter of claim 9, further comprising a guide wire lumen extending through the catheter shaft.

17. The catheter of claim 9, wherein the anode is coupled to a wall of the insulator, wherein the wall is tapered towards the anode.

18. The catheter of claim 9, wherein the insulator and the cathode define an annular region between the cathode and the insulator, the annular region being screened by the conductive coating from an electrical field generated between the anode and the cathode.

19. The catheter of claim 9, wherein the cathode is a field emission cathode.

20. The catheter of claim 19, wherein the cathode is chosen from the group consisting of graphite, titanium carbide, carbides, metals, and graphite coated with titanium carbide.

21. The catheter of claim 19, wherein the cathode comprises silicon and the x-ray unit further comprises a grid proximate the cathode.

22. The catheter of claim 19, wherein the cathode comprises silicon needles.

23. The catheter of claim 9, wherein the catheter shaft comprises a coaxial cable, the coaxial cable having an outer conductor and a central conductor, the outer conductor being electrically connected to the conductive coating.

24. The catheter of claim 23, wherein the insulator has proximal and distal ends, wherein the anode is coupled to the central conductor of the coaxial cable at the proximal end of the insulator, and wherein the cathode is coupled to the distal end of the insulator.

25. The catheter of claim 23, wherein the insulator has a substantially tubular portion having proximal and distal ends, wherein the anode is coupled to the central conductor of the coaxial cable at the proximal end of the tubular portion, and wherein the cathode is coupled to the distal end of the tubular portion.

26. The catheter of claim 23, wherein:
the coaxial cable comprises an outer conductor and a central conductor;
the insulator has a tubular portion with proximal and distal ends, the coaxial cable being coupled to the proximal end, the anode being coupled to the proximal end and to the central conductor of the coaxial cable, and the cathode being coupled to the distal end;
the catheter further comprises a conductive surface surrounding the tubular insulator, coupling the cathode to the outer conductor of the coaxial cable; and
the insulator and cathode define an annular region proximate the coupling between the cathode and the insulator, the annular region being screened from an electrical field generated between the anode and the cathode by the conductive surface and a portion of the cathode.

27. The catheter of claim 26, wherein the insulator comprises a wall depending from the proximal end of the tubular portion, the wall being angled toward the anode and the vacuum chamber.

28. The catheter of claim 9, wherein the x-ray unit has a diameter less than about 4 mm.

29. The catheter of claim 28, wherein the x-ray unit has a length less than about 15 mm.

30. The catheter of claim 23, wherein the x-ray unit has a diameter of 2.5 mm or less.

31. The catheter of claim 28, wherein the x-ray unit has a diameter of 1.25 mm or less.

32. The catheter of claim 28, wherein the x-ray unit has a diameter of about 1 mm.

33. The catheter of claim 32, wherein the x-ray unit has a length of about 7 mm.

* * * * *